United States Patent [19]

Fleenor

[11] Patent Number: 5,061,268
[45] Date of Patent: Oct. 29, 1991

[54] DISPOSABLE ELECTROSURGICAL PENCIL WITH IN-LINE FILTER AND METHOD

[75] Inventor: Richard P. Fleenor, Denver, Colo.

[73] Assignee: Beacon Laboratories, Inc., Denver, Colo.

[21] Appl. No.: 398,146

[22] Filed: Aug. 24, 1989

[51] Int. Cl.$^5$ .............................................. A61B 17/36
[52] U.S. Cl. ........................................ 606/45; 606/49
[58] Field of Search .................. 606/23, 31, 32, 41–52; 604/26, 190, 405

[56] References Cited

U.S. PATENT DOCUMENTS 4,781,175  11/1988  McGreevy et al. ............ 128/303.17
4,872,454  10/1989  DeOliveira et al. .................... 606/45

FOREIGN PATENT DOCUMENTS 8706845  11/1987  World Int. Prop. O. .......... 604/190

Primary Examiner—Max Hindenburg
Attorney, Agent, or Firm—Sheridan, Ross & McIntosh

[57] ABSTRACT

An improved electrosurgical pencil system (10) is formed with an in-line filter (32). The system (10) comprises a disposable electrosurgical pencil (12) and a disposable gas tube (14). The filter (32), which is preferably disposable, may be installed anywhere along the system (10) and is preferably positioned at the first end (30) of the tube (14). A filter material (44) comprises a length of tubular fibrous material repeatedly folded back upon itself. The material (44) is then sealed in a cylinder (46) and provided with openings (52) therein for receiving gas. The material (44) allows the gas to pass freely therethrough while preventing the passage of any particles larger than a preselected size. Thus, any bacteria larger than the preselected size are prevented from reaching the patient through the pencil system (12).

13 Claims, 2 Drawing Sheets

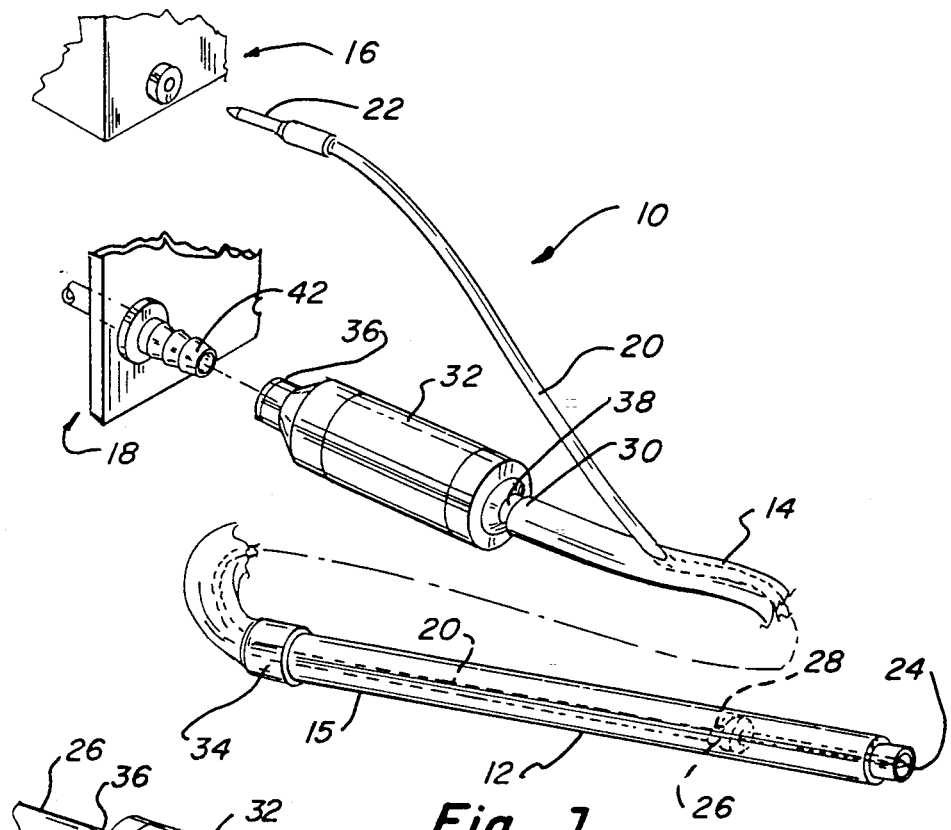
Fig_1
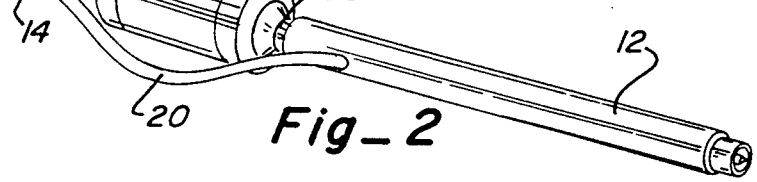
Fig_2
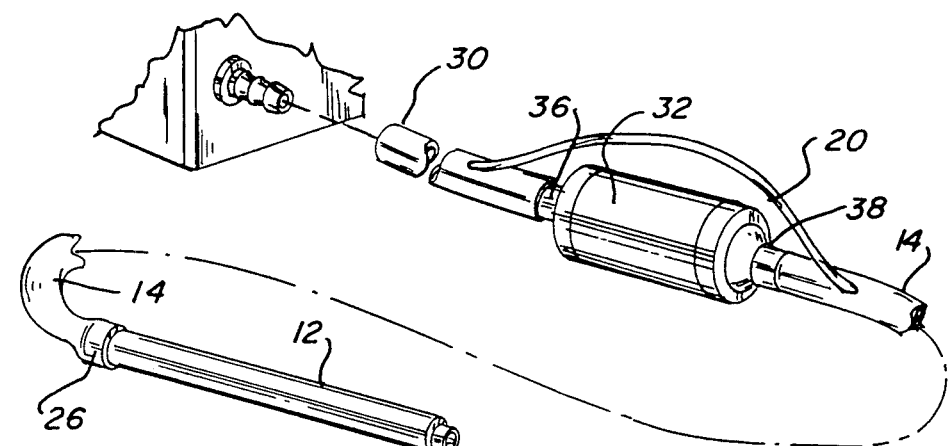
Fig_3

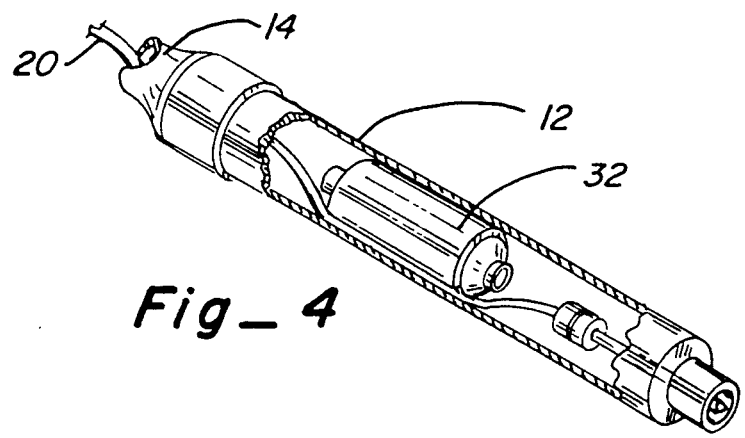
Fig_4
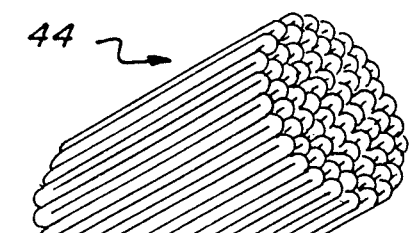
Fig_5
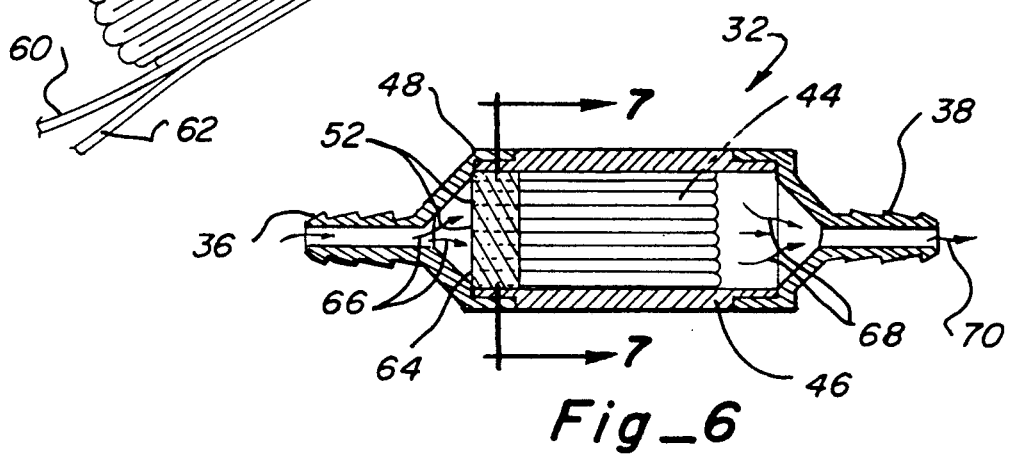
Fig_6
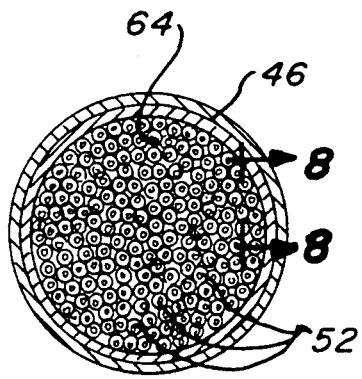
Fig_7
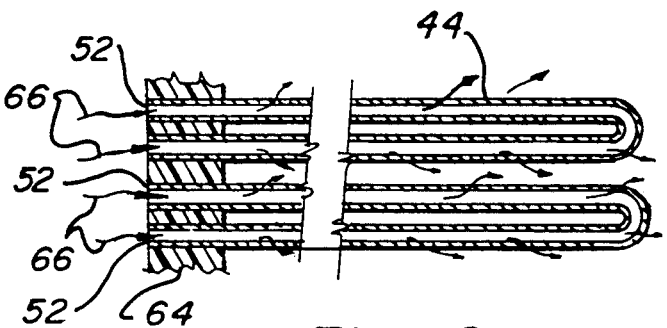
Fig_8

DISPOSABLE ELECTROSURGICAL PENCIL WITH IN-LINE FILTER AND METHOD

TECHNICAL FIELD OF THE INVENTION

This invention relates in general to electrosurgical devices, and in particular, a disposable electrosurgical pencil with an in-line filter.

BACKGROUND OF THE INVENTION

It is essential to provide a sterile environment in an operating room to prevent the furtherance of disease and infection through the transmission of bacteria to or from the patient. The techniques for sterilizing an operating room and the personnel and equipment therein have become more refined and more complex over the years, as it is no longer sufficient to merely provide sterile garments and instruments.

Surgeons and other medical personnel in an operating room are required to scrub thoroughly and to wear sterile clothing. The equipment in the operating room is generally sterilized where possible and with particular emphasis on anything coming into contact with the patient. However, the need for a sterile environment has gone beyond these long recognized minimal standards. Current trends are to provide a filtered laminar flow of air from above the operating room downward away from the operating table and out of the room. This positive pressurization attempts to force any non-sterile particles from the room.

The need to sterilize the surgical instruments obviously has been long recognized. The trend has been to provide disposable sterile products wherever possible and to thoroughly sterilize, for example, by autoclave techniques, all non-disposable articles. Since autoclave techniques are expensive (the materials that can be autoclaved are also relatively expensive), time consuming and not completely reliable, the preferred method is to use disposable instruments.

Electrosurgical techniques are frequently used in major operations to provide coagulation of blood during the surgery. It has been found that electrosurgical techniques are enhanced when an inert gas is used in conjunction with the electric charge since the inert gas allows coagulation of the blood with less desiccation of the tissue.

Electrosurgery requires the use of an electrosurgical pencil for transmitting the electric charge to the patient. Thus, the pencil must be sterile since it is proximate or in contact with the patient during surgery. If gas enhancement is used with the electrosurgery, a gas tube is included on the pencil to direct gas from a gas source to the pencil. Since the electrosurgical generator (which provides the electric charge) and the required equipment therewith cannot be completely sterilized after each use, a filter is typically provided between the gas supply and the gas tube.

One device, as provided by Bard Electronics, Inc., has a filter built into a platform between the gas source and the gas tube. The filter is fixed to a platform or unit used in electrosurgery. The electrosurgical pencil is then plugged into the platform to obtain the electric charge and the gas. Unfortunately, there is a gap between the filter and the plug-in for the pencil which allows any bacteria therein to be transmitted through the pencil by the gas. Additionally, the filter is located in a position that is not conducive to easy access for changing and can be overlooked or forgotten, whereas, it is preferable to change or clean the filter after each use to reduce the risk of contamination. In light of the drive to provide the operating room with a sterile environment, this lack of sterility in the electrosurgical instruments is generally unacceptable. Thus, there is a need for a method and apparatus to provide a sterile filter and a disposable electrosurgical pencil that eliminates the need for filtering before the pencil's gas tube.

SUMMARY OF THE INVENTION

The present invention comprises a method and apparatus for a disposable electrosurgical pencil with an in-line filter which eliminates or greatly reduces the problems associated with prior electrosurgical pencils. The present invention reduces the likelihood of the passage of bacteria from a potentially non-sterile environment to the patient through contact with an inert gas enhanced electrosurgical pencil.

In accordance with one aspect of the invention, an improved electrosurgical pencil is formed. A gas tube is connected between a gas supply and the pencil. A wire is positioned within the gas tube to interconnect the pencil to an electrosurgical generator. An in-line filter is positioned in a pre-selected location between a first end of the gas tube and a tip of the pencil. In a preferred embodiment, the filter is placed in the first end of the gas tube. In alternative embodiments, the filter may be located in the second end of the gas tube, between the first and second ends of the gas tube or within the pencil itself.

The materials used to form the improved electrosurgical pencil are preferably disposable. The filter comprises a continuous hollow tube of fibrous material folded repeatedly back upon itself to form a bundle of uniform length and a desired thickness. The filter material is preferably chosen to prevent passage therethrough of bacteria above a specific size, for example, 0.5 microns.

The bundle is then sealed within a container and provided with openings to allow the gas to flow therethrough. For example, the bundle may be placed within a cylinder having a narrowed exit designed to be received by the first end of the gas tube. A sealant, such as glue, is poured into an entrance end of the cylinder to completely cover the bundle and seal the cylinder to a predesignated depth. After the glue sets, a portion is cut radially to expose the tubular openings of the filter material. Since the cylinder itself is also sealed by the glue, the only passage for a fluid is through the tubular filter.

The entrance end of the cylinder is then covered and sealed with a narrowed entrance cap designed to be received by a gas source. Thus, as the gas enters the entrance of the cylinder, it is forced into the openings of the tubular filter material. Any particles larger than 0.5 microns are retained within the filter while the gas is allowed to pass therethrough. Only "clean" gas is therefore allowed to be passed to the electrosurgical pencil and to the patient.

BRIEF DESCRIPTION OF THE DRAWINGS

For a more complete understanding of the present invention and for further advantages thereof, reference is now made to the following Detailed Description taken in conjunction with the accompanying drawings in which:

FIG. 1 is an isometric view of an electrosurgical pencil constructed in accordance with the preferred embodiment of the present invention;

FIG. 2 is an alternative embodiment of the present invention;

FIG. 3 is an alternative embodiment of the present invention;

FIG. 4 is a further alternative embodiment of the present invention;

FIG. 5 is an isometric view of a filter material bundle in accordance with the present invention;

FIG. 6 is a cross-sectional view of a filter constructed in accordance with the preferred embodiment of the present invention;

FIG. 7 is a plan view along the line 7—7 of FIG. 6; and

FIG. 8 is a cross-sectional along the line 8—8 of FIG. 7.

DETAILED DESCRIPTION OF THE INVENTION

In FIGS. 1-8, like items are identified by like and corresponding numerals for ease of reference. Referring first to FIG. 1, an isometric view of a disposable electrosurgical pencil system constructed in accordance with the preferred embodiment of the present invention is generally identified by the reference numeral 10. The pencil system 10 comprises a disposable electrosurgical pencil 12 and a disposable gas tube 14 connected thereto. The pencil system 10 is interconnected to an electrosurgical generator generally identified by the reference numeral 16 and a gas source generally identified by the reference numeral 18.

The pencil 12 is provided with an electrical wire 20 which passes through the gas tube 14 to a cylindrical shaped pencil case 15 which preferably comprises plastic. The wire 20 is connected to the electrosurgical generator 16 at a first end 22 and to an electrode 24 at a second end 26. The electrode 24 may comprise, for example, tungsten. A plug 28 may be provided at the interface between the second end 26 of the wire 20 and the electrode 24 for connection thereto. The gas tube 14 is connected at a first end 30 to a disposable filter 32 and at a second end 34 to the electrosurgical pencil 12. The electric wire 20 exits the gas tube 14 prior to the filter 32 and is appropriately sealed to prevent leakage of gas from therearound.

The filter 32 preferably comprises a plastic cylinder with a narrowed entrance 36 and a narrowed exit 38. The narrowed entrance 36 and the narrowed exit 38 are provided for easy connection to the gas tube 14 and to the gas source 18 as well as to provide controlled flow of a gas therethrough. The gas source 18 may comprise a gas tank containing an inert gas, for example, argon. The tank may be opened by a valve (not shown) to allow the flow of gas through a connecting tube and connector 42.

Referring to FIG. 2, an alternative embodiment of the present invention is illustrated with the narrowed entrance 36 of the filter 32 installed in the second end 26 of the gas tube 14 and with the narrowed exit 38 installed onto the pencil 12. This alternative requires that the wire 20 pass through the gas tube 14 prior to the narrowed entrance 36 of the filter 32 and reenter the pencil 12 after the narrowed exit 38. This alternative embodiment obviously requires additional seals to appropriately seal around the wire 20.

Referring to FIG. 3, an additional alternative embodiment of the present invention is illustrated. In this alternative, the filter 32 is installed between the first end 30 and the second end 26 of the gas tube 14. Again, this alternative requires the electric wire 20 to pass through the gas tube 14 prior to the narrowed entrance 36 of the filter 32 and reenter the gas tube 14 after the narrowed exit 38 of the filter 32.

Referring to FIG. 4, an additional alternative embodiment is illustrated with the filter 32 installed into the pencil 12 itself. This alternative requires that the wire 20 be routed around the filter 32 in some fashion to ensure that gas does not leak through the passageway and thus circumvent the filter 32. As shown, the wire 20 may fit between the filter 32 and the pencil 12 by any appropriate means and must be sealed therein.

Referring to FIG. 5, an isometric view of a preferred embodiment of a filter material used in the filter 32 is shown. The filter material, generally identified by the reference numeral 44, preferably comprises a 0.5 micron fibrous filter material, such as is available from Microgon, Inc., Laguna Hills, Ca., under their trademark DYNAGARD. The material 44 is a continuous length of tubular fibrous material folded repeatedly back upon itself into a bundle of a uniform length. In the bundle configuration, the filter material 44 has only a first opening 60 and a second opening 62 at extreme opposite ends thereof. The filter material 44 must be inserted into a container and further processed as will be subsequently described in greater detail to form the filter 32.

Referring to FIG. 6, a filter 32 constructed in accordance with the preferred embodiment of the present invention, is illustrated. The filter 32 comprises a bundle of the filter material 44 within a plastic cylinder 46. The cylinder 46 has a narrowed exit 38 for attachment to the pencil system 10. The cylinder 46 also has a removable cap 48 with a narrowed entrance 36.

A bundle of the filter material 44 is inserted into the cylinder 46. A sealing material 64, such as polyurethane potting material, is then poured into the cylinder 46 to a predetermined depth. The sealing material 64 is allowed to cure and is then sawed or cut radially to expose a plurality of openings 52 in the filter material 44. The removable cap 48 is then sealed onto the cylinder 46 to form the filter 32. Thus, any fluid entering the filter 32 through the entrance 36 as indicated by arrows 66 must enter the openings 52 in the filter material 44. Any particles larger than the filter size, for example 0.5 microns, are captured within the tubular filter material 44 while the remaining fluid is allowed to pass therethrough and into the narrowed exit 38 as indicated by arrows 68. "Clean" gas, as indicated by arrow 70, is thus passed to the pencil 12 and the patient.

Alternatively, the filter material placed within the filter 32 may be a more conventional disk-shaped type of filter material. If disk type filter material is used, the diameter of the cylinder 46 would need to be increased in order to obtain the same flow rate as with the continuous tubular type filter.

Referring to FIG. 7, a top plan view along the line 7—7 of FIG. 6 is shown. The plurality of openings 52 are interspersed across and through the surface of the sealing material 64. Thus, it can be seen that a gas entering the filter 32 has nowhere to go except into the holes 52. Also evident from FIG. 7 is the fact that the flow rate of the gas passing through the filter 32 may be altered by installing more or less filter material 44 therein. More filter material 44 will provide a gas with an increased number of openings 52 for an increased flow rate therethrough while less filter material 44 will obviously decrease the flow rate.

Referring to FIG. 8, a partial cross-section along the line 8—8 of FIG. 7 is shown with the tubular-shaped cross-section of the filter material 44 more clearly seen. As a gas, indicated by the arrows 66, enter the holes 52 (actually the sawed ends of the material 44), the gas 66 encounters the filter material 44. Molecules and other particles smaller than the filer size, i.e., 0.5 microns, may pass directly through the material 44 anywhere therealong and eventually into the narrowed exit 38 for use with the pencil 12.

The present invention provides a disposable surgical pencil system that has an in-line anti-bacterial filter. By using the present invention, it is possible to provide a sterile electrosurgical pencil for each surgery without the fear of unrestricted bacteria from an unsterilized portion of the related equipment reaching the patient. Although not shown, it is to be understood that the improved pencil system 10 may be comprised of partially disposable and partially non-disposable materials. For example, the electrosurgical pencil 12 may comprise non-disposable materials while the tube 14 and the filter 32 are disposable. This would allow the surgical pencil 12 to be sterilized by conventional methods and still prevent the passage of bacteria from the gas source and electrosurgical generator.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. An improved electrosurgical pencil system, comprising:
   an electrosurgical pencil;
   a gas delivery means selectively connectable at a first end to an external gas source and to said electrosurgical pencil on a second end, wherein a gas is deliverable to said electrosurgical pencil for emission from an emitting end thereof towards a surgical site for enhancing electrosurgery; and
   an anti-bacterial filter positioned within the pencil system between said first end of said gas delivery means and said emitting end of said electrosurgical pencil, wherein substantially all gas deliverable through said pencil system to said surgical site is filtered to reduce the likelihood of transmission of bacteria through the pencil system to the surgical site.

2. The improved pencil system of claim 1, wherein said pencil is disposable.

3. The improved pencil system of claim 1, wherein said filter comprises a 0.5 micron fibrous filter.

4. The improved pencil system of claim 3, wherein said fibrous filter comprises a first length of hollow tubing repeatedly folded back upon itself into a uniform second length.

5. The improved pencil system of claim 1, wherein said filter is positioned at said first end of said gas delivery means.

6. The improved pencil of claim 1, wherein said filter is attached between said second end of said tube and said electrosurgical pencil.

7. The improved pencil system of claim 1, wherein said filter is positioned along said tube between said first and second ends thereof.

8. The improved pencil system of claim 1, wherein said filter is positioned within said electrosurgical pencil.

9. An improved method for filtering a gas flow to a surgical site on a patient from an electrosurgical pencil system, the pencil system having a gas delivery means selectably connectable to an external gas source on a first end and to an electrosurgical pencil on a second end, the improved method comprising the step of:
   integrally installing an anti-bacterial filter in a preselected position between the first end of the gas delivery means and an emitting end of the electrosurgical pencil wherein substantially all gas deliverable through said pencil system to said surgical site is filtered to reduce the likelihood of transmission of bacteria through the pencil system to the surgical site.

10. The improved method of claim 9, wherein the step of installing comprises:
   positioning said filter at said first end of the gas delivery means.

11. The improved pencil of claim 9, wherein the step of installing comprises:
   attaching said filter between said second end of the gas tube and the electrosurgical pencil.

12. The improved pencil of claim 9, wherein the step of installing comprises:
   attaching said filter within the tube between the first and second ends thereof.

13. The improved pencil of claim 9, wherein the step of installing comprises:
   positioning said filter within the electrosurgical pencil.

* * * * *